United States Patent [19]

Andrews

[11] 4,087,915

[45] May 9, 1978

[54] ORTHODONTIC SAFETY FACE BOW

[76] Inventor: Lawrence F. Andrews, 2025 Chatsworth Blvd., San Diego, Calif. 92107

[21] Appl. No.: 593,327

[22] Filed: Jul. 7, 1975

[51] Int. Cl.² .............................................. A61C 7/00
[52] U.S. Cl. .................................................. 32/14 D
[58] Field of Search ............................. 32/14 D, 14 A

[56] References Cited

U.S. PATENT DOCUMENTS

| 523,192 | 7/1894 | Angle | 32/14 D |
|---|---|---|---|
| 2,141,190 | 12/1938 | Linde | 32/14 A |
| 3,036,380 | 5/1962 | Martinek et al. | 32/14 D |
| 3,903,604 | 9/1975 | Snead | 32/14 D |

Primary Examiner—Robert Peshock
Attorney, Agent, or Firm—Townsend and Townsend

[57] ABSTRACT

A safety face bow having inner and outer wires, the outer wires adapted for coupling to a head cap and/or a neck pad and the inner wires adapted for terminating in an orthodontic buccal tube in which a blunt extension beyond the end of the inner wire is added for the prevention of impalement by the ends of the inner wire if the face bow assembly is pulled out of the patient's mouth. In one embodiment, the outer wire is also removably attached to the inner wire with the additional blunt edge forming a latch for retention of the inner wire should the outer wire be pulled while being worn within the patient's mouth.

2 Claims, 7 Drawing Figures

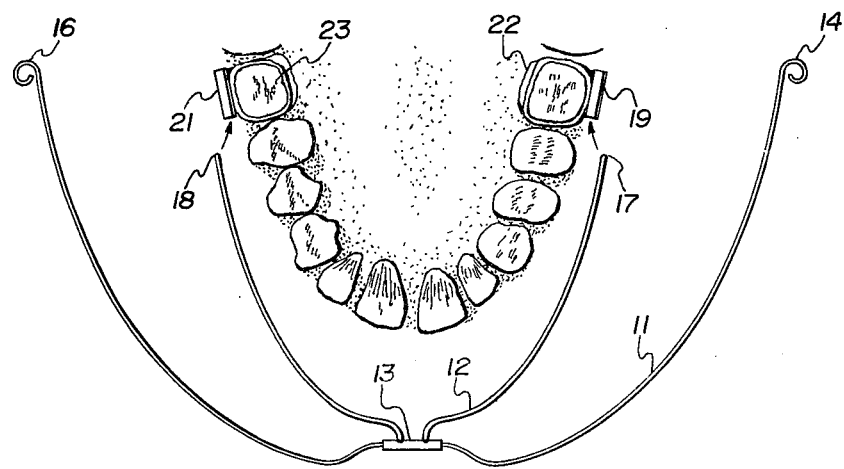
PRIOR ART Fig. 1
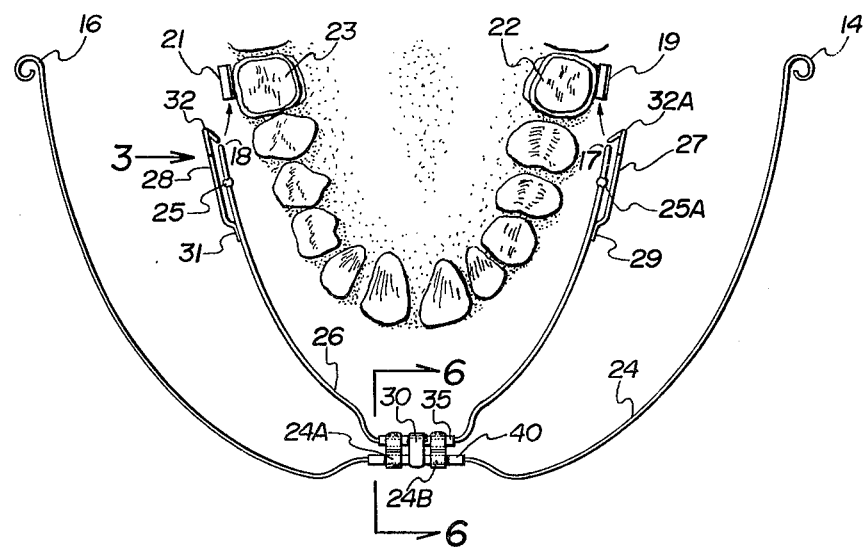
Fig. 2
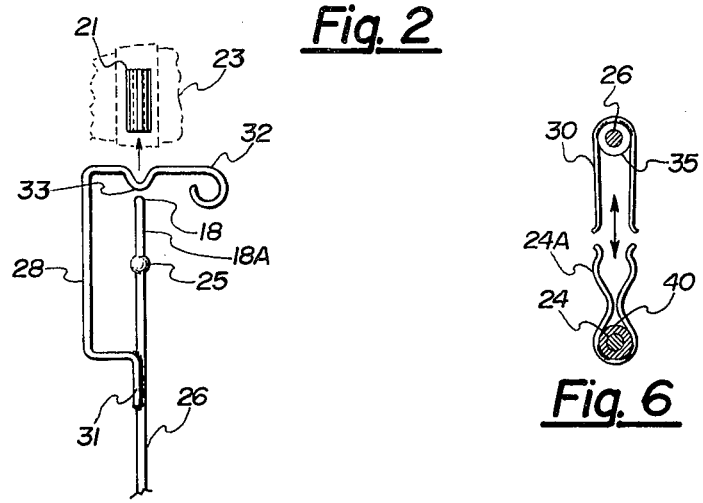
Fig. 3
Fig. 6

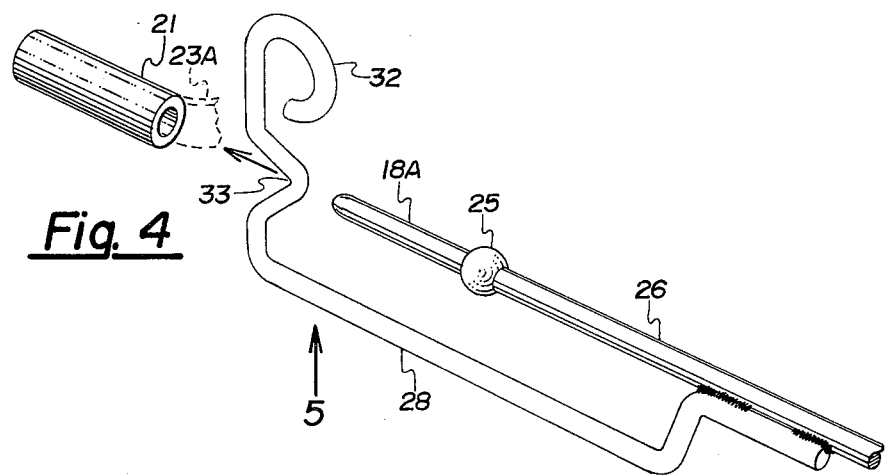
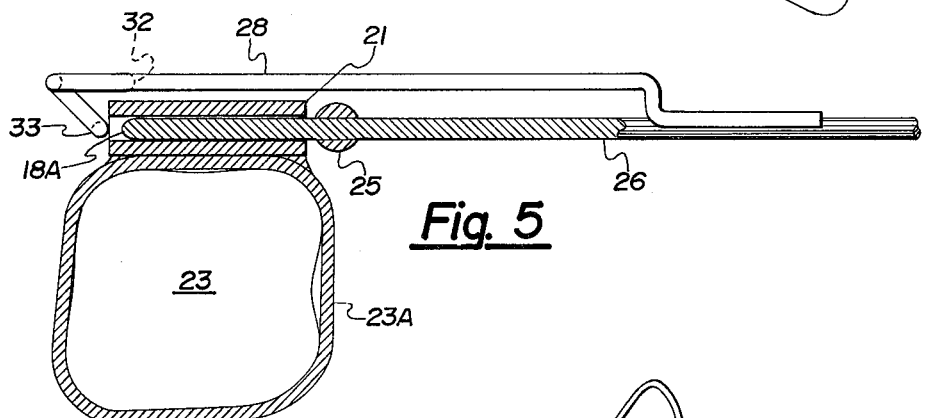
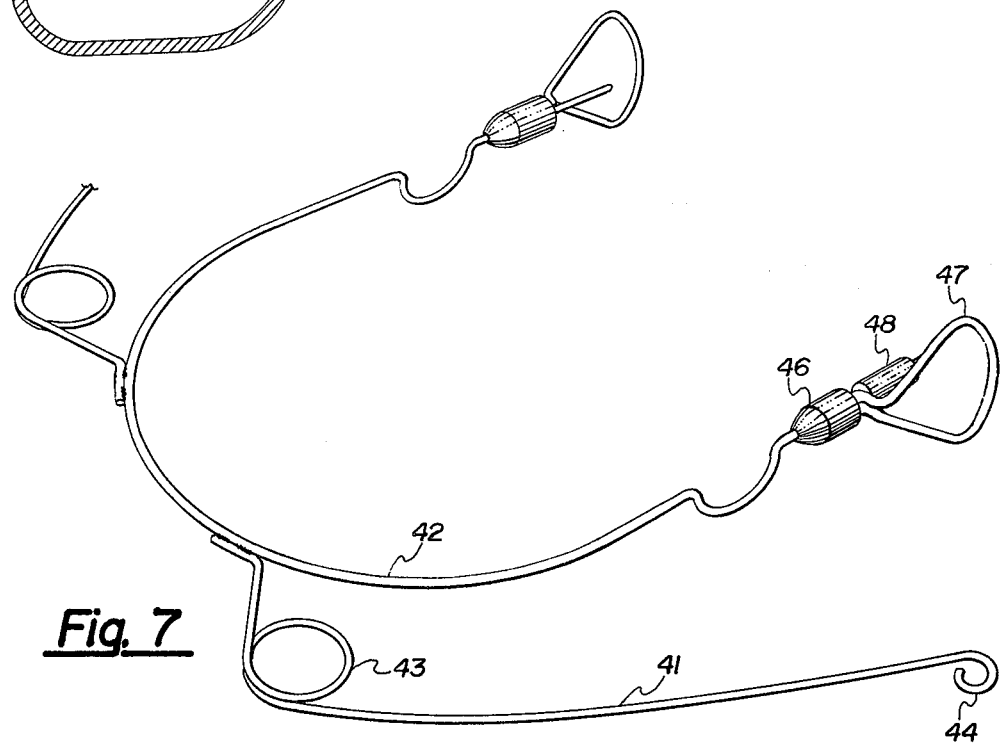

ORTHODONTIC SAFETY FACE BOW

BRIEF DESCRIPTION OF THE INVENTION

The present invention relates to an orthodontic safety face bow and more particularly to an orthodontic safety face bow for prevention of impalement by the ends of the inner wire.

According to the invention, an orthodontic face bow is provided having an outer wire for coupling to a head cap and/or a neck pad and an inner wire for terminating in a buccal tube. The prior art conventional orthodontic face bows have had the problem of exposed sharp ends of the inner wire. This can be hazardous should a small child, for example, pull the face bow out of a patient's mouth to the extent where the sharp ends are exposed and let it snap back, since the outer wire is conventionally coupled to a neck pad via elastomeric coupling means such as rubber bands. In the past this has resulted in extreme injuries to patients. The face bow of the instant application carries blunt extensions around the sharp ends of the inner wire for the prevention of impalement. Removable coupling between the inner and outer wires is also comtemplated together with a latching of the inner wire for retention of the inner wire should the outer wire be pulled while being worn by a patient.

An object of the present invention is the provision of an improved orthodontic face bow.

Another object of the invention is the provision of an orthodontic face bow with built-in safety features.

A further object of the invention is the provision of an improved orthodontic face bow which is completely safe for the patient.

Other ojbects and many of the attendant advantages of the present invention will be readily appreciated as the same becomes better understood by reference to the following detailed description when considered in connection with the accompanying drawings in which like reference numerals designate like parts throughout the Figures thereof and wherein:

FIG. 1 is a top view of a typical prior art face bow;

FIG. 2 is a top view of a preferred embodiment of the present invention;

FIG. 3 is a more detailed figure of one safety feature of FIG. 2;

FIG. 4 is a perspective view of the safety feature of FIG. 3;

FIG. 5 is a top partial view of an installed face bow of FIG. 2;

FIG. 6 is a double cross sectional view taken along lines 6—6 of FIG. 2; and

FIG. 7 is a perspective view of another embodiment of the present invention.

DETAILED DESCRIPTION OF THE DRAWING

Referring to FIG. 1, a typical prior art face bow is shown having an outer wire 11 and an inner wire 12 connected together at 13. Outer wire 11 has coupling loops 14 and 16 for coupling to a head cap and/or a neck pad and inner wire 12 has sharp ends 17 and 18 dimensioned for being received by buccal tubes 19 and 21 attached to rear molars 22 and 23.

Referring to FIG. 2, an orthodontic archwire is shown having an outer wire 24 terminating in coupling loops 14 and 16 for coupling to a head cap and/or a neck pad. Outer wire 24 is removably coupled to inner wire 26 which terminates at sharp ends 17 and 18. Inner wire 26 carries a guide tube 35 with guide extension 30 extending therefrom. Outer wire 24 carries a guide tube 40 dimensioned for being received by guide extension 30. Guide tube 40 also carries spring clamps 24A dimensioned for clamping guide tube 35. Solder stops 25 and 25A are dimensioned for limiting the reception of the inner wire 26 into buccal tubes 19 and 21 which are attached to rear molars 22 and 23, respectively. Safety extensions 27 and 28 are coupled to inner wire 26 at 29 and 31, respectively.

Referring to FIG. 3, a portion of inner wire 26 is shown having an end portion 18A extending beyond solder stop 25. Safety extension 28 coupled to inner wire 26 at 31 terminates in a loop portion 32 and has a latch detent 33 dimensioned for latching at the end of buccal tube 21.

Referring to FIG. 4, a portion of inner wire 26 terminates in portion 18A which is dimensioned for being received by buccal tube 21 up to a solder stop 25. Safety extension 28 terminates in a loop 32 and has a detent 33 for latching at the end of buccal tube 21.

Referring FIG. 5, rear molar 23 carries a band 23A which in turn carries buccal tube 21. Buccal tube 21 receives end portion 18A of inner wire 26 up to solder stop 25. Safety extension 28 has a detent portion 33 which latches onto the end of buccal tube 21.

Referring to FIG. 6, inner wire 26 carries a guide tube 35 with guide extension 30 extending therefrom. Outer wire 24 carries a guide tube 40 dimensioned for being received by guide extension 30. Guide tube 40 also carries spring clamps 24A dimensioned for clamping guide tube 35.

Referring to FIG. 7, outer wire 41 is attached as by soldering to inner wire 42. Outer wire 41 has a spring loop 43 and terminates in a coupling loop 44 to a head cap and/or a neck pad. Inner wire 42 passes through mounting tubes 46 which fixedly carry safety loops 47. Mounting tubes 46 can be fixedly attached to inner wire 42 and abut buccal tubes 48 through which the ends of inner wire 42 are passed.

OPERATION

Referring back to FIG. 1, it can be seen that if coupling loops 14 and 16 are elastomerically coupled to a head cap and/or a neck pad and inner wire 12 is mounted within the patient's mouth, someone pulling at the portion around coupling 13 could pull the entire assembly out of the patient's mouth and away from the patient's face, whereby, upon releasing the assembly, sharp ends 17 and 18 of inner wire 12 can impale the patient's face. The purpose of the invention is to obviate this problem.

Referring to FIGS. 2, 3, 4, 5, and 6, one embodiment of the invention is shown in which the sharp ends 17 and 18 of inner wire 26 are surrounded by safety loops 32A and 32 of safety extensions 27 and 28, respectively. Hence, if the assembly were pulled out of the patient's mouth and released, these safety loops reduce the possibility of an impalement by sharp ends 17 and 18 of inner wire 26. To further reduce this possibility, latching detents 33 are dimensioned for being received by the ends of buccal tubes 19 and 21 so that upon pulling outer wire 24, the spring clamps 24A will decouple outer wire 24 from inner wire 26, resulting in sharp ends 17 and 18 of inner wire 26 remaining in place.

Referring to FIG. 7, a modification is shown utilizing a safety loop 47 having its ends captured within coupling tube 46 with inner wire 42 passing therethrough. On installation, the ends of inner wire 42 are passed through coupling tubes 46 and then through buccal tubes 48. The positioning of coupling tubes 46 is determined and the face bow removed at which time the positions of coupling tubes 46 on inner wire 42 can be fixed as by soldering or left for slight movement on inner wire 42. The assembly is reinserted in the patient's mouth with the ends of inner wire 42 protruding through buccal tubes 48. At this time, the loops 47 can be further adjusted for patient comfort. It can be seen that if the assembly were pulled out of the patient's mouth and released, the safety loops 47 would prevent serious injury to the patient.

It should be understood, of course, that the foregoing disclosure relates to only a preferred embodiment of the invention, and that it is intended to cover all changes and modifications of the example of the invention herein chosen, for the purposes of the disclosure, which do not constitute departures from the spirit and scope of the invention.

The invention claimed is:

1. In an orthodontic safety face bow composed of:
   an inner wire and an outer wire, said inner wire and outer wire being coupled together at central portions thereof, said outer wire having first and second ends adapted for coupling to a head cap and/or a neck pad, said inner wire having first and second ends adapted for being received by buccal tubes; the improvement comprising
   first and second safety extensions being coupled at one end to said inner wire and extending freely beyond said inner wire's first and second ends, respectively, terminating in looped portions through a location which intersects an extension of the axis of respective of said first and second ends so that when said inner ends said safety extensions each including a detent portion at said locations for engaging with said buccal tubes are positioned to extend through one end of said buccal tubes, said safety extensions will engage the other end of respective of said buccal tubes and prevent displacement of said inner wire therefrom.

2. The orthodontic safety face bow of claim 1 wherein:
   said inner wire and outer wire are removably coupled together.

* * * * *